United States Patent [19]

Wong

[11] Patent Number: 5,021,528
[45] Date of Patent: Jun. 4, 1991

[54] CROSSLINKED BISPHENOL CONTAINING ARYLCYCLOBUTENE ALKYL ETHERS AND CURED COMPOSITIONS THEREFROM

[75] Inventor: Pui K. Wong, Katy, Tex.

[73] Assignee: Shell Oil Company, Houston, Tex.

[21] Appl. No.: 503,415

[22] Filed: Mar. 30, 1990

Related U.S. Application Data

[63] Continuation-in-part of Ser. No. 349,546, May 9, 1989, Pat. No. 4,943,665.

[51] Int. Cl.$^5$ .................... C08F 10/00; C08F 32/08; C08G 59/00
[52] U.S. Cl. ........................................ 526/280; 528/86
[58] Field of Search ...................... 526/280; 528/86

[56] References Cited

U.S. PATENT DOCUMENTS

| | | | |
|---|---|---|---|
| 4,450,763 | 9/1985 | Kirchhoff | 526/281 |
| 4,642,329 | 2/1987 | Kirchhoff et al. | 528/396 |
| 4,791,182 | 12/1988 | Kirchhoff et al. | 528/396 |
| 4,943,665 | 7/1990 | Wong | 568/633 |

*Primary Examiner*—Morton Foelak
*Assistant Examiner*—T. Mosley

[57] ABSTRACT

Novel, cured compositions are obtained by heating self-curing ethers produced from di(hydroxyphenyl) compound and an arylcyclobutenealkyl compound. The di(hydroxyphenyl) compound di(arylcyclobutenealkyl) ethers cure upon heating to produce rigid thermosets of relatively high glass transition temperature and heat stability.

9 Claims, No Drawings

CROSSLINKED BISPHENOL CONTAINING ARYLCYCLOBUTENE ALKYL ETHERS AND CURED COMPOSITIONS THEREFROM

RELATED APPLICATION

This application is a continuation-in-part of copending U.S. patent application Ser. No. 349,546 filed May 9, 1989, now U.S. Pat. No. 4,943,665.

FIELD OF THE INVENTION

This invention relates to certain ether derivatives of di(hydroxyphenyl) compounds. More particularly, the invention relates to cured products produced from arylcyclobutenealkyl ethers of di(hydroxyphenyl) compounds upon application of heat.

BACKGROUND OF THE INVENTION

The curing of monomeric materials to produce polymeric thermoset resins is well known in the art. In general, the polymerizable monomers have at least one and customarily more than one reactive group which serves as an active site for a curing or crosslinking polymerization to produce the thermoset resins. However, crosslinking of many or most polymerizable monomers, for example the curing of epoxy resins, requires the use of a curing agent, catalytic or stoichiometric, to cause the curing or crosslinking to occur at an acceptable rate. Even in the presence of most curing agents the rate of crosslinking is slower than desired and the addition of an accelerator is required to obtain sufficiently rapid curing. Some monomers will cure at an acceptable rate in the absence of curing agent but only upon application of high intensity energy, e.g., UV light.

There are other monomers wherein the active site is such that no additional curing agent or high intensity energy is necessary and the monomers will cure upon application of heat. Such monomers are termed "self-curing". One class of such monomers includes within the molecular structure moieties of an arylcyclobutene, for example, a benzocyclobutene. Without wishing to be bound by any particular theory, it appears likely that upon application of heat the cyclobutene ring undergoes ring-opening to produce active intermediates which crosslink by undergoing reaction with adjacent molecules. The resulting resins have properties of rigidity and strength.

A series of U.S. patents to Kirchhoff, illustrated by U.S. Pat. No. 4,540,763, describes the production of a large number of benzocyclobutene derivatives including ethers of di(hydroxyphenyl) compounds such as di(hydroxyphenyl)alkanes or bisphenol alkanes, wherein the ether oxygen directly links the phenyl ring of the di(hydroxyphenyl) compound to the six-membered ring of the benzocyclobutene group, as well as the cured products produced therefrom. The benzocyclobutene derivatives of Kirchhoff are characterized by this direct link of a functional group between the benzocyclobutene moiety and the rest of the molecule.

A copending U.S. patent application, Ser. No. 349,547, filed May 9, 1989, relates to certain arylcyclobutene ester derivatives of polymeric materials wherein the carboxy function is connected to the arylcyclobutene moiety through an alkylene group. Such compositions are also self-curing. It would be of advantage to provide cured compositions of arylcyclobutene derivatives of di(hydroxyphenyl) compounds where the ether oxygen is connected to the arylcyclobutene moiety through an alkylene group. Such cured compositions are hard resins having good properties.

SUMMARY OF THE INVENTION

This invention provides a class of cured products produced from ether derivatives of di(hydroxyphenyl) compounds by self-curing of the ethers. More particularly, the invention relates to the hard resins produced by the self-curing of arylcyclobutenealkyl ethers of the di(hydroxyphenyl) compounds upon application of heat.

DESCRIPTION OF THE INVENTION

The novel cured products of the invention are produced from arylcyclobutenealkyl ethers of a di(hydroxyphenyl) compound, wherein the ether oxygen atoms connect the phenyl ring of the di(hydroxyphenyl) compound with the arylcyclobutene moiety through an alkylene group attached to a carbon atom of a six-membered ring of the arylcyclobutene group, upon application of heat. The ethers are produced by reaction of an arylcyclobutenealkyl compound with a metal salt, particularly an alkali metal salt, of the di(hydroxyphenyl) compound.

The di(hydroxyphenyl) compounds which are suitably employed as precursors of the compositions of the invention have up to 30 carbon atoms and from 1 to 2 aromatic rings, inclusive. When two aromatic rings are present, the rings are fused or are connected by a direct valence bond, alkylene of up to 8 carbon atoms inclusive, oxy, thio, carbonyl, carboxyl or carbonato. One class of such di(hydroxyphenyl) compounds is represented by the formula

wherein X has up to 30 carbon atoms and from 1 to two aromatic rings which, when two rings are present are fused or joined as described above and has at least one hydroxyl substituent on each aromatic ring. The moiety X in formula I is otherwise hydrocarbyl containing only atoms of carbon and hydrogen besides any additional atoms present in divalent joining groups or is substituted hydrocarbyl containing additional atoms present as unreactive carbon atom substituents, e.g., halogen, preferably the middle halogens chloro or bromo. Illustrative di(hydroxyphenyl) compounds of formula I include hydroquinone, resorcinol, 1,5-dihydroxynaphthalene, 4,4'-dihydroxy-2,2'-dimethylbisphenyl, 2,2-di(4-hydroxyphenyl)propane, di(4-hydroxyphenyl)methane, 2,2-bis(4-hydroxy-3,5-dibromophenyl)propane, di(3-hydroxyphenyl) ether, di(4-hydroxy-3-ethylphenyl) ketone or di(4-hydroxyphenyl) carbonate.

A preferred class of di(hydroxyphenyl) compounds is represented by the formula

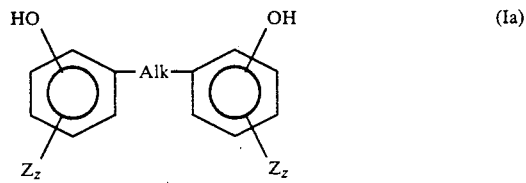

wherein Alk is alkylene of up to 8 carbon atoms inclusive, Z independently is alkyl, preferably lower alkyl of up to 4 carbon atoms inclusive, or halo, preferably middle halo, and z independently is an integer from 0 to inclusive, preferably from 0 to 2 inclusive. Such di(hydroxyphenyl) compounds are illustrated by di(3-hydroxyphenyl)methane, 1,1-di(4-hydroxy-2-methylphenyl)ethane, 2,2-di(4-hydroxyphenyl)propane, 4,4-di(4-hydroxy-3-chlorophenyl)octane, 2,2-bis(4-hydroxy-3,5-dibromophenyl)butane. The preferred hydroxyl substitution is on ring carbon atoms para to the carbon atom connected to the Alk group and z is most preferably zero. The compound 2-2-di(4-hydroxyphenyl)propane, also known as bisphenol A or BPA, is a particularly preferred di(hydroxyphenyl) compound. The di(hydroxyphenyl) compounds are known compounds or are prepared by known methods.

The arylcyclobutenealkyl compounds which are employed as reactants in the production of the self-curing ethers are represented by the formula $$Ar-R-W \tag{II}$$

wherein Ar is an arylcyclobutene group, R is alkylene of up to 4 carbon atoms inclusive and W is an electron-withdrawing group.

Suitable W groups in the above formula 11 are those which, when attached to an aromatic ring are thought to be ring deactivating and meta-directing or, expressed differently, are those groups commonly referred to as good "leaving groups" in nucleophilic substitution reactions. Preferred W groups are upper halo, i.e., halogens other than fluoro (chloro, bromo or iodo), or sulfonic ester such as aryl sulfonate, e.g., tosylate, brosylate or nosylate, alkyl sulfonate, e.g., mesylate, and fluoroalkyl sulfonate, e.g., triflate or nonaflate. The term R of formula II is alkylene of up to 4 carbon atoms, e.g., methylene, 1,2-ethylene or 1,4-butylene, but preferably is methylene.

The arylcyclobutene group Ar is an aromatic ring system of up to aromatic rings and up to 30 carbon atoms, inclusive, which contains at least one cyclobutene ring fused to an aromatic ring. Suitable aromatic ring systems are illustrated by the single aromatic ring system compound benzene, the fused aromatic ring system compounds naphthalene, anthracene and phenanthrene, the directly joined ring system compounds of two or more aromatic rings joined by an alkylene group of up to 8 carbon atoms inclusive, e.g., diphenylalkanes such as diphenylmethane and 2,2-diphenylpropane. The preferred aromatic ring system is the single aromatic ring compound benzene and the preferred arylcyclobutene moiety is a benzocyclobutene moiety. The Ar moiety is hydrocarbyl containing only atoms of carbon and hydrogen or is substituted hydrocarbyl containing additional atoms as inert carbon atom substituents, e.g., cyano or middle halo. The preferred Ar group is a benzocyclobutene group.

In the most preferred embodiment of producing the ethers, the arylcyclobutenealkyl compound is a halomethylbenzocyclobutene of the formula

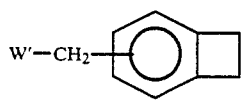
(IIa)

wherein W' is upper halo, i.e., chloro, bromo or iodo, but preferably is chloro or bromo, especially chloro. The halomethylbenzocyclobutenes are prepared by one of several reaction schemes depending upon the desired spacial arrangement of the halomethyl substituent and the cyclobutene ring. A 4-halomethylbenzocyclobutene is prepared from p-methylbenzyl halide, preferably p-methylbenzyl chloride, in two steps according to the procedure of Ewing et al, J. Chem. Soc. Chem. Comm., 1979, 207. Preparation of 3-chloromethylbenzocyclobutene is effected by a similar procedure starting with o-methylbenzyl chloride. In this case, however, the procedure yields about a 1:2 molar mixture of 3-chloromethylbenzocyclobutene and 4-chloromethylbenzocyclobutene. This mixture is separated into its individual components by conventional methods such as distillation or chromatographic separation or alternatively is used as such without separation of the isomers. Other arylcyclobutenealkyl compounds are also known compounds or are produced by known methods.

The arylcyclobutenealkyl compound is reacted with a metal salt of the di(hydroxyphenyl) compound. Although other metal salts of the di(hydroxyphenyl) compound are useful in the process of the invention, the preferred metal salts are alkali metal salts and lithium, sodium, potassium, rubidium and cesium salts are satisfactory. Among the alkali metal salts, sodium or potassium salts are the more suitable, particularly sodium salts. In one modification, the alkali metal salt is produced, isolated and employed as a preformed material. In this modification, the di(hydroxyphenyl) compound is contacted with a strong alkali metal base, e.g., an alkali metal hydroxide, carbonate or bicarbonate, preferably hydroxide, in an inert reaction diluent in which the alkali metal salt of the di(hydroxyphenyl) compound is at least partially soluble. Water is generally satisfactory for this purpose. The alkali metal base and the di(hydroxyphenyl) compound are provided in a ratio of equivalents from about 1:1 to about 10:1 although ratios from about 1:1 to about 4:1 are generally preferred. Reaction takes place at moderate temperatures, for example, from about 15° C. to about 30° C. in a non-gaseous phase. Subsequent to reaction, the alkali metal salt of the di(hydroxyphenyl) compound is isolated by conventional techniques such as solvent removal, precipitation or selective extraction.

In the preferred embodiment of the process of producing the ethers, the alkali metal salt of the di(hydroxyphenyl) compound is formed in situ and is utilized, without isolation, in the reaction with the arylcyclobutenealkyl compound. Because of the difficulty of employing a reaction solvent or diluent in which both the alkali metal salt and the arylcyclobutenealkyl compound are both soluble, the reaction is typically conducted in a two-phase system employing a first diluent and a second diluent in which the arylcyclobutenealkyl compound is soluble. The first diluent is preferably the diluent in which the alkali metal salt is to be formed and water is a suitable first diluent. The second diluent is an organic reaction diluent and is preferably an aromatic hydrocarbon such as benzene, toluene or xylene. To facilitate the reaction which takes place at the interface of the two phases, a phase transfer agent is customarily employed. Such agents are often tetraalkylammonium salts wherein each alkyl independently is up to 12 carbon atoms inclusive. Illustrative of tetraalkylammonium salts are tetramethylammonium chloride, tetrabutylammonium bromide, methyltrihexylammonium bicarbonate, trimethyldodecylammonium bisulfate, ethyltriheptylammonium sulfate and tetrapropylammonium chloride. The preferred salts are tetrabutylammonium salts, especially tetra-n-butylammonium salts, especially tetra-n-butylammonium chloride. Also suitable as phase transfer agents is the class of macrocyclic polyethers of the type known as "crown ethers" and other types of phase transfer agents are known in the art as is the utilization of a phase transfer agent. Tetraalkylammonium salts are the preferred phase transfer agents.

In this "in situ" modification of the process of ether production, the reaction is typically conducted by mixing an aqueous solution of the alkali metal base, the di(hydroxyphenyl) compound and the phase transfer agent with a solution of the arylcyclobutenealkyl compound in the second diluent. Reactant contact at the phase interface is facilitated by vigorous agitation as by stirring or refluxing. Reaction conditions include reaction temperatures that are from about 10° C. to about 150° C. but preferably are from about 25° C. to about 100° C. The reaction pressure that is suitable is that which is sufficient to maintain the reaction mixture in a non-gaseous phase. Such pressures are typically up to about 20 atmospheres but more often are from about 0.8 atmosphere to about 5 atmospheres. Subsequent to reaction, the arylcyclobutenealkyl ether of the di(hydroxyphenyl) compound is recovered by well-known methods such as precipitation or solvent removal.

The self-curing ethers of the invention are bis(arylcyclobutenealkyl) ethers of the di(hydroxyphenyl) compound wherein each phenolic hydrogen of the di(hydroxyphenyl) compound has been replaced by an arylcyclobutenealkyl moiety. In terms of the reactants of formula I and formula II the ether products are represented by the formula Ar—R—O—X—O—R—Ar     (III)

wherein Ar, R and X have the previously stated meanings. In terms of the preferred reactants of formula Ia and formula IIa, the ether products are represented by the formula

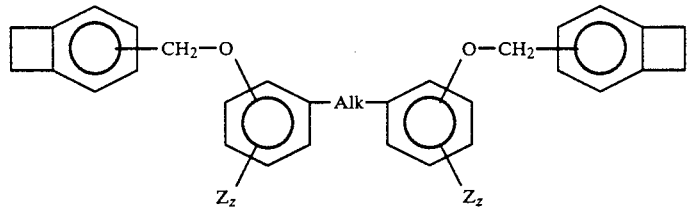

wherein Z, z and Alk have the previously stated meanings.

The nomenclature of the ether precursors of the cured products of the invention is difficult because of the complexity thereof but illustrative ethers include 2,2-di(4-hydroxyphenyl)propane di(4-benzocyclobutenylmethyl) ether illustratively produced by reaction o the sodium salt of 2,2-di(4-hydroxyphenyl)propane and 4-chloromethylbenzocyclobutene and 1,5-dihydroxynaphthalene di[2-(3-benzocylobutenyl)ethyl] ether illustratively produced by reaction of the potassium salt of 1,5-dihydroxynaphthalene and 3-(2-bromoethyl)benzocyclobutene. The identity of other ethers will be apparent from consideration of the above formulas for the reactants (formulas I and II) and for the products (formula III).

The di(arylcyclobutenealkyl) ethers of the di(hydroxyphenyl) compound are generally viscous liquids or low melting solids depending in part on the purity of the product and whether a single arylcyclobutenealkyl compound isomer or a mixture of isomers was employed in the production of the ether. The ethers are characterized by stability and a long shelf-life at ambient temperature. The ethers are self-curing or are cured without the presence of added accelerators by heating the ether to an elevated temperature, typically above about 150° C. to about 250° C. The cured products have relatively high glass (transition temperatures, often over 200° C., and are rigid thermosets with good tensile strength. The cured products are processed by methods conventional for curing monomeric materials to thermoset resins and find utility in applications such as coating materials and structural materials in the aerospace and electronic industries.

The invention is further illustrated by the following Illustrative Embodiments which should not be regarded as limiting the invention.

ILLUSTRATIVE EMBODIMENT I

To a solution of 2,2-di(4-hydroxyphenyl)propane (2.26 g, 9.9 mmol), sodium hydroxide (3.96 g, 99 mmol) and tetra-n-butylammonium bisulfate (0.61 g, 1.8 mmol) in 30 ml of water was added a solution of 4-chloromethylbenzocyclobutene (3 g, 19.8 mmol) in 30 ml of toluene. The mixture was heated at 65° C. for 7 hours and then extracted with diethyl ether. The ether extract was washed with water and dilute aqueous sodium bicarbonate, dried over magnesium sulfide and evaporated under reduced pressure. The product, 4.55 g, a 100% yield, was a viscous off-white oil which solidified on standing. The $^1$H—NMR and $^{13}$C—NMR spectra were consistent with the structure 2,2-di(4-hydroxyphenyl)propane di(4-benzocyclobutenemethyl) ether.

ILLUSTRATIVE EMBODIMENT II

The procedure of Illustrative Embodiment 1 was repeated except that an approximately 1:2 molar mixture of 3-chloromethylbenzocyclobutene and 4-chloromethylbenzocyclobutene was employed in place of the 4-chloromethylbenzocyclobutene. The product, a viscous yellow oil, was a mixture of 2,2-di(4-hydroxyphenyl)propane ethers, the etherifying groups being 4-benzocyclobutenemethyl, 3-benzocyclobutenemethyl and mixtures thereof.

ILLUSTRATIVE EMBODIMENT III

The product mixture of Illustrative Embodiment II was heated at 200° C. for 24 hours under nitrogen. The product of the heating was a yellow, clear and rigid thermoset with a glass transition temperature of 218° C. as determined by Differential Scanning Calorimeter (DSC) methods. By Thermal Gravimetric Analysis (TGA), employing a heating rate of 10° C./minute, the temperature of onset of weight loss was found to be 432° C.

ILLUSTRATIVE EMBODIMENT IV

When the ether product of Illustrative Embodiment I is heated to a temperature above 150° C., a hard thermoset resin will be obtained.

What is claimed is:

1. The rigid, crosslinked product obtained by heating to a temperature above about 150° C. the ether of the formula Ar—R—O—X—O—R—Ar wherein Ar is an aromatic ring system of up to 30 carbon atoms and up to 4 aromatic rings inclusive having a cyclobutene ring fused to at least one of the aromatic rings, R is alkylene of up to 4 carbon atoms and inclusive and X has up to 30 carbon atoms and from 1 to 2 aromatic rings which, when two rings are present, are fused or are joined by a direct valence bond or alkylene of up to 8 carbon atoms inclusive, oxy, thio, carbonyl, carboxyl or carbonate, wherein each R is attached to a carbon atom of a six-membered aromatic ring.

2. The rigid, crosslinked product of claim 1 wherein the ether is represented by the formula

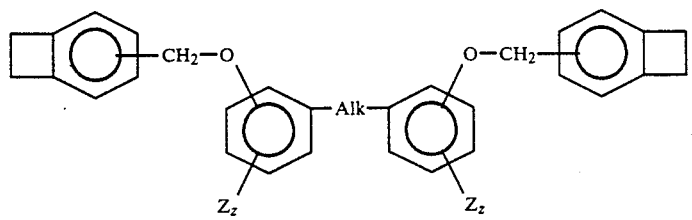

wherein Alk is alkylene of up to 8 carbon atoms inclusive, Z independently is alkyl or halo and z independently is an integer from 0 to 4 inclusive.

3. The rigid, crosslinked product of claim 2 wherein the temperature of heating is from above about 150° C. to about 250° C.

4. The rigid, crosslinked product of claim 3 wherein Z is halo and z is an integer from 0 to 2 inclusive.

5. The rigid, crosslinked product of claim 4 wherein Z is bromo.

6. The rigid, crosslinked product of claim 2 wherein Z is alkyl.

7. The rigid, crosslinked product of claim 2 wherein each z is zero.

8. The rigid, crosslinked product of claim 7 wherein the oxygens of the ether are substituted on rIng carbon atoms para to the ring carbon atoms attached to Alk.

9. The rigid, crosslinked product of claim 8 wherein the ether is 2,2-di(4-hydroxyphenyl) di(4-benzocyclobutenemethyl) ether.

* * * * *